United States Patent
Franssen et al.

(10) Patent No.: US 12,162,054 B2
(45) Date of Patent: *Dec. 10, 2024

(54) COMPOSITIONS AND METHODS FOR CLEANING CONTAMINATED SOLIDS AND LIQUIDS

(71) Applicants: Todd Franssen, Dacono, CO (US); Carla Franssen, Dacono, CO (US)

(72) Inventors: Todd Franssen, Dacono, CO (US); Carla Franssen, Dacono, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/213,528

(22) Filed: Jun. 23, 2023

(65) Prior Publication Data

US 2023/0330727 A1 Oct. 19, 2023

Related U.S. Application Data

(63) Continuation of application No. 17/150,500, filed on Jan. 15, 2021, now Pat. No. 11,724,293, which is a continuation of application No. 16/111,409, filed on Aug. 24, 2018, now Pat. No. 10,906,075, which is a continuation-in-part of application No. 15/196,212, filed on Jun. 29, 2016, now Pat. No. 10,065,224, which is a continuation of application No. 14/456,912, filed on Aug. 11, 2014, now Pat. No. 9,403,198.

(60) Provisional application No. 61/864,040, filed on Aug. 9, 2013.

(51) Int. Cl.

| | |
|---|---|
| *B09C 1/10* | (2006.01) |
| *B09C 1/00* | (2006.01) |
| *B09C 1/08* | (2006.01) |
| *C02F 1/28* | (2023.01) |
| *C02F 1/68* | (2023.01) |
| *C02F 3/00* | (2023.01) |
| *C02F 3/34* | (2023.01) |
| *C12N 1/20* | (2006.01) |
| *C02F 101/32* | (2006.01) |
| *C02F 103/06* | (2006.01) |
| *C02F 103/36* | (2006.01) |

(52) U.S. Cl.
CPC ................ *B09C 1/10* (2013.01); *B09C 1/00* (2013.01); *B09C 1/002* (2013.01); *B09C 1/08* (2013.01); *C02F 1/288* (2013.01); *C02F 1/681* (2013.01); *C02F 3/00* (2013.01); *C02F 3/341* (2013.01); *C02F 3/343* (2013.01); *C12N 1/20* (2013.01); *B09C 2101/00* (2013.01); *C02F 1/281* (2013.01); *C02F 1/283* (2013.01); *C02F 1/286* (2013.01); *C02F 2003/001* (2013.01); *C02F 3/342* (2013.01); *C02F 3/344* (2013.01); *C02F 3/347* (2013.01); *C02F 3/348* (2013.01); *C02F 2101/322* (2013.01); *C02F 2103/06* (2013.01); *C02F 2103/365* (2013.01); *C02F 2209/06* (2013.01); *C02F 2305/04* (2013.01)

(58) Field of Classification Search
CPC .. B09C 1/10; B09C 1/00; B09C 1/002; B09C 1/08; B09C 2101/00; C02F 1/288; C02F 1/681; C02F 3/00; C02F 3/341; C02F 3/343; C02F 1/281; C02F 1/283; C02F 1/286; C02F 3/342; C02F 3/344; C02F 3/347; C02F 3/348; C02F 2003/001; C02F 2101/322; C02F 2103/06; C02F 2103/365; C02F 2209/06; C02F 2305/04; C12N 1/20

See application file for complete search history.

(56) References Cited

U.S. PATENT DOCUMENTS

| | | | |
|---|---|---|---|
| 5,139,365 | A | 8/1992 | Chesner |
| 5,265,674 | A | 11/1993 | Fredrickson et al. |
| 5,401,413 | A | 3/1995 | Gatt et al. |
| 5,464,766 | A | 11/1995 | Bruno |
| 5,476,788 | A | 12/1995 | Lamar et al. |
| 5,486,474 | A | 1/1996 | Bradley et al. |
| 5,508,194 | A | 4/1996 | Lee et al. |
| 5,536,407 | A | 7/1996 | Petersen |
| 5,885,602 | A | 3/1999 | Levy |
| 5,939,086 | A | 8/1999 | Levy |
| 5,990,067 | A | 11/1999 | Franssen et al. |
| 6,194,197 | B1 | 2/2001 | Hyman et al. |
| 6,251,657 | B1 | 6/2001 | Hunter et al. |

(Continued)

FOREIGN PATENT DOCUMENTS

| | | |
|---|---|---|
| EP | 0234626 | 9/1987 |
| EP | 1081099 | 3/2001 |

(Continued)

OTHER PUBLICATIONS

Evans et al., "Degradation of plant cell wall polymers," Fungi in Bioremediation, 2001, Fungi in Bioremediation, Cambridge University Press, Cambridge, U.K., 24 pages.

(Continued)

*Primary Examiner* — David W Berke-Schlessel
*Assistant Examiner* — Susan E. Fernandez
(74) *Attorney, Agent, or Firm* — Sheridan Ross P.C.

(57) ABSTRACT

The present invention relates to compositions and methods for the remediation of contaminated solids and liquids. In particular, embodiments of the present invention relate to the bioremediation of solids and liquids by a composition comprising a biocatalyst or mixture of biocatalysts. The present invention also relates to methods for producing the bioremediation compositions and methods for applying the bioremediation compositions to contaminated sites, including treatment, storage, and disposal facilities, as well as various contaminated water sources, such as aquifers and reservoirs.

5 Claims, No Drawings

(56) References Cited

U.S. PATENT DOCUMENTS

| | | |
|---|---|---|
| 6,503,746 B1 | 1/2003 | Daane et al. |
| 6,511,954 B1 | 1/2003 | Wilbur et al. |
| 6,773,625 B2 | 8/2004 | Falk et al. |
| 6,814,816 B2 | 11/2004 | Achar et al. |
| 6,969,699 B1 | 11/2005 | Sen et al. |
| 7,056,061 B2 | 6/2006 | Kukor et al. |
| 7,071,153 B2 | 7/2006 | Lewis et al. |
| 7,459,421 B2 | 12/2008 | Bullis et al. |
| 7,658,805 B2 | 2/2010 | Netherton |
| 7,906,320 B2 | 3/2011 | Lu et al. |
| 8,133,855 B2 | 3/2012 | Dreilinger et al. |
| 8,197,605 B2 | 6/2012 | Laffitte et al. |
| 8,206,062 B2 | 6/2012 | Hoag et al. |
| 8,444,962 B2 | 5/2013 | Helmke et al. |
| 9,403,198 B1 | 8/2016 | Franssen et al. |
| 10,065,224 B2 | 9/2018 | Franssen et al. |
| 10,906,075 B2 | 1/2021 | Franssen et al. |
| 11,724,293 B2 | 8/2023 | Franssen et al. |
| 2002/0187545 A1 | 12/2002 | Calcavecchio et al. |
| 2003/0100098 A1 | 5/2003 | Haggblom et al. |
| 2004/0126882 A1 | 7/2004 | Ellington et al. |
| 2007/0002994 A1 | 1/2007 | Kanter et al. |
| 2007/0003994 A1 | 1/2007 | Simpson et al. |
| 2007/0068685 A1 | 3/2007 | Arnott et al. |
| 2008/0070231 A1 | 3/2008 | Franciskovich et al. |
| 2010/0209988 A1 | 8/2010 | Hutchings et al. |
| 2010/0274069 A1 | 10/2010 | Kumar et al. |
| 2012/0094360 A1 | 4/2012 | Fuhrer |
| 2013/0023037 A1 | 1/2013 | Kiely et al. |

FOREIGN PATENT DOCUMENTS

| | | |
|---|---|---|
| EP | 1352694 | 5/2008 |
| FR | 2874618 | 3/2006 |
| GB | 2351502 | 1/2001 |
| WO | WO 94/29242 | 12/1994 |
| WO | WO 95/08513 | 3/1995 |
| WO | WO 99/46210 | 9/1999 |
| WO | WO 99/66080 | 12/1999 |
| WO | WO 00/41976 | 7/2000 |
| WO | WO 01/58607 | 8/2001 |
| WO | WO 03/080787 | 10/2003 |
| WO | WO 2004/090156 | 10/2004 |
| WO | WO 2005/042724 | 5/2005 |
| WO | WO 2006/018306 | 2/2006 |
| WO | WO 2006/136177 | 12/2006 |
| WO | WO 2013/022332 | 2/2013 |

OTHER PUBLICATIONS

Heitzer et al., "Specific and Quantitative Assessment of Naphthalene and Salicylate Bioavailability by Using a Bioluminescent Catabolic Reporter Bacterium," Applied and Environmental Microbiology, vol. 58, No. 6, Jun. 1992, pp. 1839-1846.

Jia et al., "A Critical Review of Naphthalene Sources and Exposures Relevant to Indoor and Outdoor Air," International Journal of Environmental Research and Public Health, vol. 7, 2010, pp. 2903-2939.

Norton, "Fungi for Bioremediation of Hydrocarbon Pollutants," 2012, vol. 10, retrieved from http://hilo.hawaii.edu/academics/hohonu/documents/Vol10x06FungiforBioremediationofHydrocarbonPollutants.pdf, pp. 18-21.

Rud-Hansen, "Enzymes at Work," Novozymes, 2011, retrieved from http://www.novozymes.com/en/about-us/brochures/documents/enzymes_at_work.pdf, 64 pages.

Vidali, "Bioremediation. An overview," Pure Appl. Chem., 2001, vol. 73(7), pp. 1163-1172.

Official Action for U.S. Appl. No. 14/456,912, dated Jan. 29, 2016, 14 pages.

Official Action for U.S. Appl. No. 14/456,912, dated Mar. 9, 2016, 17 pages.

Notice of Allowance for U.S. Appl. No. 14/456,912, dated Apr. 5, 2016, 9 pages.

Official Action for U.S. Appl. No. 15/196,212, dated Oct. 19, 2017, 17 pages.

Notice of Allowance for U.S. Appl. No. 15/196,212, dated May 2, 2018, 9 pages.

Official Action for U.S. Appl. No. 16/111,409, dated Apr. 6, 2020, 11 pages.

Notice of Allowance for U.S. Appl. No. 16/111,409, dated Sep. 30, 2020, 9 pages.

Official Action for U.S. Appl. No. 17/150,500, dated Sep. 29, 2022, 12 pages.

Notice of Allowance for U.S. Appl. No. 17/150,500, dated Mar. 27, 2023, 8 pages.

COMPOSITIONS AND METHODS FOR CLEANING CONTAMINATED SOLIDS AND LIQUIDS

CROSS-REFERENCE TO RELATED APPLICATIONS

The present application is a continuation of U.S. patent application Ser. No. 17/150,500, filed Jan. 15, 2021, which is a continuation of U.S. patent application Ser. No. 16/111,409, filed Aug. 24, 2018 (now U.S. Pat. No. 10,906,075, issuing Feb. 2, 2021), which is a continuation-in-part of U.S. patent application Ser. No. 15/196,212, filed Jun. 29, 2016 (now U.S. Pat. No. 10,065,224, issuing Sep. 4, 2018), which is a continuation of U.S. patent application Ser. No. 14/456,912, filed Aug. 11, 2014 (now U.S. Pat. No. 9,403,198, issued Aug. 2, 2016), which claims the benefit of U.S. Provisional Patent Application Ser. No. 61/864,040, filed Aug. 9, 2013, the entire content of which is hereby incorporated by reference herein.

FIELD OF THE INVENTION

The present invention relates to compositions and methods for the remediation of contaminated solids and liquids, in particular the bioremediation of solids and liquids by a composition comprising a biocatalyst or mixture of biocatalysts.

BACKGROUND OF THE INVENTION

Chemical contamination of the environment, particularly of soil and groundwater is currently a widespread problem that is prevalent in many parts of the industrialized world. Industrial pollution has contaminated millions of acres of soil and associated aquifers. Over the past several decades worldwide production, processing, storage, transportation and utilization of synthetic and naturally occurring chemical substances has led to the introduction of significant quantities of hazardous materials into the environment. Unintentional spillage of petroleum, industrial solvents, food and animal wastes and other substances has been caused, for example, by weathering, chemical corrosion and accidental damage to pipes, storage vessels, processing equipment, transportation vehicles, etc. Deliberate acts and carelessness have also contributed to the release of hazardous substances into the environment. The spillage of such materials has resulted in large numbers of polluted sites and enormous volumetric quantities of soil and groundwater which have been contaminated with hazardous substances. Soil contamination can cause extensive damage to the local ecosystem by accumulating in the tissue of animals and plants, and by causing death thereto and/or mutation to the progeny thereof. Such contamination can also present a serious health threat to humans and, in extreme cases, can render the contaminated area unsuitable for human habitation. In many cases, contaminated sites can pose a danger to adjacent property, such as by entrainment of hazardous substances by local groundwater flow, and local laws frequently mandate remediation prior to the sale or lease of property wherein the soil has been contaminated with hazardous materials.

Unfortunately, clean up of such contaminated sites and spills is extraordinarily difficult, and can be extremely labor intensive, costly and time consuming. Oil spills, especially involving water, are particularly troublesome to treat, as are oil producing well sites contaminated with crude oil. Existing cleaning technologies were often developed prior to the current environmentally-conscientious market. As such, environmentally harmful potentials such as runoff, toxicity, acid-base balances, and other downstream effects were seen in existing products. Technological improvements to existing cleaning products remained minor since large companies failed to recognize the growing market need for a suitable cleaning product applicable to soils, water, and hard surfaces.

The biological treatment or bioremediation of waste water, soil, oil spills, refinery waste, and other contaminants has been attempted in the past, but most technologies are fraught with complications and disadvantages. Some of these efforts have attempted to utilize bacteria, fungi or other microbes to biodegrade the contaminants, into more environmentally friendly materials, but most technologies have accompanying disadvantages and limitations.

Further, various microbial products were introduced with the concept of degrading the contaminants rather than simply transferring the problem from one site to another. To this end, enzymes were often added to existing products. However, since enzymes only perform within narrowly defined ranges of contaminants, the enzymes often ceased working once the contaminants were only partially degraded; leaving behind residue and secondary contaminants that could be as problematic as the original contaminant.

For example, European Patent No. 1352694, which is incorporated by reference herein in its entirety, discloses a method for the bioremediation of soils using a compost material derived from plant material, biological sludges, urban waste, animal manure, and combinations of bacteria, and/or molds in a liquid broth. This solution has some potential disadvantages such as difficult raw material handling and a final remediation agent that is limited to the treatment of soils. In addition the composting step may require a significant amount of time to produce the target remediation product, and the wide variation in the composting raw materials will likely result in broad variability in the bioremediation agent's final bioactivity and the composition of its final microbial flora.

U.S. Pat. No. 5,265,674 ("the '674 Patent") describes a method for the remediation of aquifers comprising injecting a liquid oil into the contaminated site, wherein the oil may further comprise microorganisms and nutrients. This method may be problematic if the oil itself does not degrade and subsequently accumulates in the aquifer. Further the method is somewhat limited in that it appears to be limited to the treatment of contaminated water sources. Finally, this method is applied as a liquid, which has spill hazards and complex, costly application methods. PCT Application WO 99/46210 and U.S. Patent Application Publication No. 2013/0023037 also describe composting methods, and both potentially suffer from the same disadvantages as the '674 Patent.

Some methods for remediating soils that utilize in situ techniques such as aeration, venting and air sparging are generally limited to contaminants having a relatively high vapor pressure. Compounds such as polycyclic aromatic hydrocarbons, which have a low-vapor pressure, cannot be successfully removed by volatilization. Moreover, conventional bioremediation techniques utilizing indigenous microorganisms alone or in combination with genetically altered exogenous microorganisms is not always effective for degrading certain types of recalcitrant contaminants which are strongly resistant to biodegradation. Genetically engineering microbes is also time consuming and expensive and may result in a strain that is capable of achieving a desired metabolic function, but is weakened in other key metabolic areas, resulting in a strain that is ineffective or cost-prohibitive in large-scale production and use.

In addition, many of the present techniques for remediating soils and water take long periods of time to reduce the contaminants to acceptable or non-detectable limits. Faster treatment times of larger contaminated areas or volumes is a long-standing need in industry, that has the potential to reduce the cost of bioremediation, as well as the lost opportunity costs of land and resources that cannot be used due their contaminated state.

Thus, while various known techniques are available for the disposal or reclamation of contaminated soil, such methods do not generally provide a practical, affordable technology for remediating soil and water sources in reasonable periods of time. Accordingly, there is a need for simple, inexpensive, environmentally acceptable methods and means for remediating soils and water, within time spans on the order of days, instead of many months or even years.

SUMMARY OF THE INVENTION

It is therefore one aspect of embodiments of the present invention to provide a remediation biocatalyst composition that is effective at removing a wide variety of contaminants from contaminated solids and liquids, in particular contaminated soils and water supplies, such as ground water and aquifers. It is an aspect of embodiments of the invention to provide biocatalyst compositions and methods of use for the remediation of large scale contaminated soil and ground water sites that quickly reduce the contaminants to acceptable levels, allowing the resources to once again enter normal use or consumption, wherein remediation times are on the order of days to months, rather than on the order of years. It is another aspect of embodiments of the invention to provide compositions and methods for the remediation of contaminated soils and water supplies that are simple and cost-effective from both manufacturing and use perspectives. Another aspect of embodiments of the present invention is to provide a partially dry composition, which has advantages over liquid compositions including reduced spill hazards and simpler, less costly application methods. It is yet another aspect of embodiments of the present invention to provide compositions that utilize readily available materials, including unwanted industrial by-product streams and/or agricultural by-product streams.

It is one aspect of embodiments of the present invention to provide a new product that not only remediated surfaces esthetically but actually reduced or eliminated the organic contaminants responsible for the problem, and could also be used over a wide variety of applications including water and soil remediation. Living bacterial systems are capable of switching on and off enzyme genes to produce a wide variety of the correct enzymes as the contaminants and the conditions changed. However, no one organism can breakdown all contaminants to the final desirable end points (such as water and harmless nitrogen gas). Simply combining all of the various microbes that can individually breakdown the various components proved ineffective probably because of competitive interactions between the various species of bacteria. Finding the right microbial "team" is only a portion of the problem with remediation products; there are other requirements that must be met for an environmentally friendly, yet effective, decontamination. Microbes function by producing exterior enzymes that breakdown molecules outside of their cellular walls, which can be transferred into the organism to be further broken down inside the cells.

Effective storage and shipping of mass-blended microorganisms was also difficult and frequently lead to nonviable organisms. Though liquid formulations had some ease of application benefits, their freeze/thaw problems and short cast of available players (amenable to the necessary preservation techniques) limited their widespread application. Dried bacterial products offered many advantages to problems encountered in the oncoming "microbial revolution." If the species can be preserved as a spore, it can withstand harsh shipping and storage conditions and has an extended life span that can cover centuries. Thus, it is one aspect of embodiments of the invention to provide a dry bioremediation formula that can be shipped and stored and contain viable organisms. Furthermore, many organisms can be freeze dried which further increases the possible array of microbial candidates.

It is one aspect of embodiments of the present invention to provide a bioremediation formula with microbes and surfactants. A microbe working exclusively on the surface of a spill will be too slow in their breakdown efforts be effective. Such an application requires the contaminants to be removed and blended to be more available to the microbes. With the addition of a surfactant, smaller spherical suspensions of contaminants are produced that can be attacked by the appropriate microbes from all directions at once rather than merely on a flat surface.

It is another aspect of embodiments of the present invention to provide a bioremediation formula with a co-absorbent to capture and hold the intermediate breakdown byproducts for further degradation. These short-lived secondary intermediates can otherwise escape and avoid further degradation. A co-absorbent allows the organisms in the product to continue the break-down pathway to a desirable end-point.

One aspect of embodiments of the present invention is to provide a bioremediation formula with an abrasive ingredient to help physically remove the contaminant as well as buffers, and other items, known to add complimentary properties to the entire product. Microbial candidates, co-absorbents, abrasives, and supporting nutrient are selected for the bioremediation formula with full consideration of environmental impact implications. Where possible, naturally occurring items (such as cotton, sand, corn and chalk) are selected to meet those needs. Using recycled waste products, such as fly ash and kiln dust, are also used as environmentally friendly components. PCT Patent Publication No. WO 03/080787 to Sen et al. discloses using fly ash as an abrasive ingredient in a scouring powder composition and is incorporated by reference herein in its entirety. U.K. Patent Publication No. GB 2 351 502 to Salem also disclosing cleaning materials including fly ash and is incorporated by reference herein in its entirety.

The bioremediation composition may be an emulsion comprising multiple ingredients. The emulsion can be similar to the one described in U.S. Pat. No. 6,511,954 to Wilburn et al., which is incorporated by reference herein in its entirety.

Because the action of embodiments of the bioremediation formula results in a complex and dynamic living system that is constantly changing, the exact identity of the enzymes and the exact role of any one ingredient at any one time is also changing and may be indeterminable; but the blend of living organisms create a choreography of synergistic living organisms all playing together as an effective team to degrade the contaminant. One embodiment of the formulation enhances the bioavailability to the included microbes.

It is one aspect of embodiments of the present invention to provide a bioremediation composition that can work with or without water and that can work on water and ice. Thus, in one embodiment, the bioremediation composition functions by pulling water out of the atmosphere; therefore, the bioremediation process is accelerated when water is added to the bioremediation composition or when the bioremediation composition is used on water or ice.

It is a further aspect of embodiments of the present invention to provide a method of producing a bioremediation composition using biological hosts to synthesize/accumulate bioproducts such as bacteria, eukaryotic microorganisms (e.g., *Saccharomyces cerevisiae*), plants, animal cells (e.g., transformed insect cells growing in culture), and animals. For example, methods by which effector-sensitive RCANAs can be used to facilitate industrial biosynthesis and bioremediation are included herein. U.S. Patent Publication No. 2004/0126882 to Ellington et al. is incorporated by reference herein in its entirety.

An aspect of the present invention includes a composition for the remediation of contaminated soils or water supplies comprising an oxide phase, a silicate phase, a pH adjustment agent, a densification agent, a nutrient, a surfactant, and a biocatalyst, wherein contacting the contaminated soil or water with said composition results in a visual color change of said contaminated soil or water after seven days of said composition being spread on said contaminated soil or water.

A further aspect of the invention includes a composition for the remediation of contaminated liquids or solids comprising an oxide phase between about 20 wt % and about 40 wt %, a silicate phase between about 5 wt % and about 25 wt %, a pH adjustment agent between about 1 wt % and about 20 wt %, and a densification agent between about 1 wt % and about 20 wt %. The composition further comprises a nutrient between about 1 wt % and about 10 wt %, a surfactant between about 1 wt % and about 10 wt % and a microbial agent between about 10 wt % and about 30 wt %.

Yet another aspect of the present invention includes a composition for the remediation of contaminated liquids or solids comprising between about 20 wt % and about 40 wt % fly ash, between about 10 wt % and about 20 wt % Portland cement kiln dust, between about 5 wt % and about 15 wt % sand, between about 0.5 wt % and about 4 wt % milled whole kernel corn, between about 0.5 wt % and about 4 wt % milled cotton hulls, between about 5 wt % and about 15 wt % calcium carbonate, between about 2 wt % and about 10 wt % grout, between about 1 wt % and about 10 wt % detergent, and between about 10 wt % and about 30 wt % of biocatalyst. The biocatalyst comprises between about 5 wt % and about 15 wt % *Bacillus amyloliquefaciens*, between about 5 wt % and about 15 wt % *Bacillus atrophaeus*, between about 5 wt % and about 15 wt % *Bacillus benzeovorans*, between about 5 wt % and about 15 wt % *Bacillus cereus*, between about 5 wt % and about 15 wt % *Bacillus licheniformis*, between about 5 wt % and about 15 wt % *Bacillus megaterium*, between about 20 wt % and about 25 wt % *Bacillus subtilis*, between about 5 wt % and about 15 wt % *Bacillus polymyxa*, between about 5 wt % and about 15 wt % *Micrococcus flavus*, and between about 5 wt % and about 15 wt % *Micrococcus conglomeratus*.

In some embodiments of the present invention, the composition may further comprise a particle size of less than 0.125 inches. In some embodiments of the present invention, the composition may further comprise a moisture content of less than 15 wt %. In one embodiment of the invention, contacting the contaminated solids or liquids with said composition results in a visual color change of said contaminated solids or liquids after seven days of said composition being spread on said contaminated solids or liquids In various embodiments of the present invention a bioremediation composition is provided with traces of perfumes, charcoal, and/or odor absorbing compounds.

In one embodiment, the composition comprises a urea hydrochloride, a surfactant, and a glycol ether. Glycol ethers are miscible with water and retain their solvent properties in water solutions. The composition may also include a corrosion inhibitor to protect the surface being cleaned. Further, essential oils (such as terpene), terpene hydrocarbons, petroleum distillates, and/or di-basic esters may be added to the composition.

In some embodiments, the composition is in the form of a solid, gel, solution, paste, or a powder.

This Summary of the Invention is neither intended nor should it be construed as being representative of the full extent and scope of this disclosure. Moreover, references made herein to "the present invention" or aspects thereof, should be understood to mean certain embodiments and should not necessarily be construed as limiting all embodiments to a particular description. The present invention is set forth in various levels of detail in the Summary of the Invention as well as in the Detailed Description and Examples and no limitation as to the scope is intended by either the inclusion or non-inclusion of elements, components, etc. in this Summary of the Invention. Additional aspects will become more readily apparent from the Detailed Description, particularly when taken together with the examples.

DETAILED DESCRIPTION

The following detailed description illustrates the invention by way of example and not by way of limitation. This description will clearly enable one skilled in the art to make and use the invention. To reduce the need to provide extensive disclosure in this application, but to provide adequate written description of the various devices and methods encompassed by the numerous embodiments of the present invention, various patents are incorporated herein in their entireties by reference.

References in the specification to "one embodiment", "an embodiment", "an example embodiment", "some embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein, the term "remediation" refers to a process whereby contaminants are degraded from a first concentration to a second lower concentration. This is typically from a first unacceptable contaminated concentration, to a second acceptable concentration that more closely approaches a normal, naturally occurring background level. In some embodiments of the present invention, remediation may use living organisms or microbes, for example microorganisms, to degrade or transform environmental contaminants into less toxic forms. This is referred to as "bioremediation." Bioremediation is a subset of remediation.

As used herein, the term "contaminant" refers to any undesirable chemical or compound that is present at some level in a bulk solid, liquid, or gas. Examples of contaminants processed by the present invention include, but are not limited to, chemicals, petroleum, oils, toxins, and poisons. Contaminants are typically man-made, manufactured compounds including, but not limited to, petroleum products, hydrocarbons, oils, greases, synthetic chemicals, pesticides, herbicides and the like. Other examples of contaminants that may be treated by some embodiments of the present invention include, but are not limited to, chlorinated solvents, polychlorinated biphenyls, chlorinated phenols, benzene, toluene, ethylbenzene, xylene, and polyaromatic hydrocarbons (PAHs). Still further examples of contaminants include, but are not limited to, food waste, meat processing waste, animal-by-products, agricultural waste, biological waste, hospital waste, blood product waste, sewage, algae, and various post-consumer wastes.

As used herein, the term "hydrocarbon" refers to compounds comprising hydrogen and carbon. The term also refers to compounds comprising hydrogen, carbon and oxygen, as well as compounds comprising hydrogen, carbon, oxygen and at least one other element.

As used herein, the term "oil" refers to a liquid mixture of a variety of hydrocarbons. Such mixtures may comprise, for example, volatile compounds, saturated hydrocarbons, and/or aromatic hydrocarbons. Volatile compounds may comprise low molecular weight compounds, like methane (natural gas) or propane that are normally gaseous or evaporate very quickly at room temperature. Saturated hydrocarbons may comprise compounds with carbon and hydrogen atoms connected only by single bonds. Saturated hydrocarbons can be arranged in straight or branched chains of up to and even greater than 25 carbon atoms. Saturated hydrocarbons may be readily remediated although degradability tends to decrease with chain length. Aromatic compounds may comprise compounds that contain rings of carbon atoms held together with double bonds between the carbon atoms. The smallest aromatic compounds in petroleum have six carbons in such a ring structure (e.g., benzene and toluene), but other compounds contain multiple rings. These are polycyclic aromatic hydrocarbons (PAH). Most aromatic molecules in petroleum have multiple attached hydrocarbon chains. The smallest aromatic molecules (one- and two-rings) are both volatile and readily biodegraded, even with attached side-chains. However, four-ring and larger aromatic compounds tend to be more resistant to remediation. The percentage of PAHs in crude oil varies, but the 'priority pollutants' are present at low levels in crude oils; they are much more common as a byproduct of burning carbonaceous materials such as fuel, coal, wood, tobacco and other materials. Asphaltenes are examples of high molecular weight PAHs that have additional chemical side chains attached to their aromatic rings. Asphaltenes are not soluble in water and most organic solvents. The term "oil" also refers to larger molecular weight molecules including, but not limited to, crude, diesel fuel, jet fuel and other even higher molecular weight compounds. These may be saturated, unsaturated, cyclic, straight-chained or branched molecules.

As used herein, the term "surfactant" refers to nonionic surfactants, cationic surfactants, anionic, and amphoteric surfactants. Examples of nonionic surfactants that may be utilized in some embodiments of the present invention include, but are not limited to, are alkoxylated alkyl phenols, amides, amines, ethoxylated or propoxylated higher aliphatic alcohols, and sulphonamides. These surfactants include sorbitan esters of C10 to C22 fatty acids, polyoxyethylene sorbitan esters of C10 to C22 fatty acids, polyoxyethylene sorbitol esters of C10 to C22 fatty acids, polyoxyethylene derivatives of C6 to C20 fatty phenols, and polyoxyethylene condensates of C10 to C22 fatty acids or fatty alcohols. Other suitable nonionic surfactants include sorbitol monolaurate propylene oxide condensates, sorbitol monomyristate propylene oxide condensates, sorbitol monostearate propylene oxide condensates, dodecyl phenol propylene oxide condensates, myristyl phenol propylene oxide condensates, octylphenyl propylene oxide condensates, nonylphenyl propylene oxide condensates, stearyl phenol propylene oxide condensates, lauryl alcohol propylene oxide condensates stearyl alcohol propylene oxide condensates, secondary alcohol propylene oxide condensates such as C14-C15 secondary alcohols condensed with propylene oxide, sorbitan tristearate condensed with propylene oxide, sorbitan trioleate condensed with propylene oxide, and sorbitan trioleate, and polyoxyethylene and polyoxypropylene analogs of the above surfactants.

Examples of cationic surfactants include, but are not limited to, quaternary ammonium surfactants such as C10 to C22 fatty ammonium compounds, C10 to C22 fatty morpholine oxides, propylene oxide condensates of C10 to C22 fatty acid monoesters of glycerins, the mono- or diethanol amides of C10 to C22 fatty acids, and alkoxylated siloxane surfactants containing propylene oxide units and/or propylene oxide units. As is known in the surfactant art, the counterion for quaternary ammonium surfactants is usually a halide, sulfate, or methylsulfate, the chlorides being the most common industrially available compounds. Other suitable cationic surfactants suitable for use in the present invention include straight chain alkyl fatty amines, quaternary ammonium salts, alkyl-substituted quaternary ammonium salts, alkylaryl-substituted quaternary ammonium salts, quaternary imidazolinium salts, amine oxides, fatty amine oxides, tri-fatty amine oxides, tri-quaternary phosphate esters, amphoglycinate phosphates, amine acetates, long chain amines and their salts, diamines and their salts, polyamines and their salts, polyoxyethylenated long chain amines, and quaternized polyoxyethylenated long chain amines.

Examples of anionic surfactants include, but are not limited to, alkali metal, ammonium and magnesium salts of alpha olefin sulfonates, alkyl sulfonates, alkylaryl sulfonates, alkylaryl ether sulfates, alkylether sulfates, sulfated alcohol ethoxylates, taurates, petroleum sulfonates, alkylnapthalene sulfonates, alkylsarcosinates and the alkylsulfosuccinates. Further examples of anionic surfactants include, but are not limited to, sodium lauryl sulfonate, ammonium lauryl sulfonate, dodecyl benzene sulfonate, sodium lauryl ether sulfate, diethanolamine lauryl sulfate, ammonium salts of sulfated alcohol ethoxylates, sodium cocoyl isethionate, sodium N-methyl-N-oleoyl taurate, sodium N-methyl-N-cocyl taurate, triethanolamine lauryl sulfate, disodium monooleamide PEG-2 sulfosuccinate, petroleum sulfonate sodium salt, alkyl napthalene sodium sulfonates, sodium lauroyl sarcosinate, and sodium alkyl sulfosuccinate. Other useful anionic surfactants include sodium or potassium dodecyl sulfate, sodium trioleate, sodium or potassium stearyl sulfate, sodium or potassium dodecyl benzene sulfonate, sodium or potassium stearyl sulfonate, triethanol amine salt of dodecyl sulfate, sodium laurate, sodium or potassium myristate, and sodium or potassium stearate.

Examples of amphoteric surfactants include, but are not limited to, betaines, sultaines, imidazoline derivatives and the like. Specific amphoteric surfactants useful in the present invention include ricinoleamidopropyl betaine, cocamidopropylbetaine, stearyl betaine, stearyl amphocarboxy glycinate, sodium lauraminopropionate, cocoamidopropyl hydroxysultaine, disodium lauryliminodipropionate, tallowiminodipropionate, cocoamphocarboxy glycinate, cocoimidazoline carboxylate, lauric imidazoline monocarboxylate, lauric imidazoline dicarboxylate, lauric myristic betain, cocoamidosulfobetaine, alkylamidophosphobetain and the like. Further examples of useful amphoteric surfactants include decyl amino betaine, coco amido sulfobetaine, oleyl amido betaine, coco imidazoline, coco sulfoimidazoline, cetyl imidazoline, 1-hydroxyethyl-2-heptadecenylimidazoline, 1-hydroxyethyl-2 mixed heptadecenyl heptadecadienyl imidazoline, and n-coco morpholine oxide.

As used herein, the term "detergent" refers to a surfactant or a mixture of surfactants. A detergent may assist with the physical interaction between two or more unlike components, for example oil and water, by stabilizing the interface between the two components.

As used herein, the term "bleaching agent" refers to a compound which removes color, whitens and/or disinfects. As used herein, bleaching may occur via oxidation or reduction reactions. Examples of bleaching agents that may be utilized in that may be used in some embodiments of the present invention include, but are not limited to, sodium hypochlorite, calcium hypochlorite, peroxides, hydrogen peroxide, sodium percarbonate, sodium perborate, sodium dithionite, sodium borohydride, peracetic acid, and benzoyl peroxide. Examples of solid bleaching agents are disclosed in U.S. Pat. No. 6,773,625 to Falk et al. and European Patent Application Publication No. 0234626, both of which are incorporated by reference in their entirety herein.

As used herein, the term "pH adjustment agent" refers a chemical, compound or material that is used to manipulate or adjust the pH of a mixture. Examples of pH adjustment agents that may be used in some embodiments of the present invention include, but are not limited to, acids which may be used to lower the pH of a mixture or composition with a starting value that is relatively high. Alternatively, further examples of pH adjustment agents include, but are not limited to, bases which may be used to raise the pH of a mixture or composition with a starting value that is relatively low. pH adjustment may be critical in systems defined primarily by chemical reactions in the absence of enzymes and microbes. However, pH adjustment may also be important in defining the optimum pH for maximum enzyme activities and microbial growth and metabolic rates.

Examples of pH adjustment agents that may be used in some embodiments of the present invention include various acids, which may be weak acids, strong acids, mineral acids, or organic acids. A strong acid is defined as an acid that completely disassociates in water, whereas a weak acid does not. Examples of acids include, but are not limited to, selenic acid, selenious acid, silicofluoric acid, telluric acid, tellurous acid, tungstic acid, xenic acid, citric acid, formic acid, pyroantimonic acid, permanganic acid, antimonous acid, antimonic acid, hypofluorous acid, phthalic acid, antimonous acid, silicic acid, titanic acid, arsenic acid, perpechnetic acid, hypophosphoric acid, pyrophosphoric acid, hydroarsenic acid, dichromic acid, tetraboric acid, metastannic acid, hypooxalous acid, glutamic acid, cyanic acid, silicous acid, fluorous acid, ferricyanic acid, malonic acid, fluoric acid, hydrocyanic acid, and thiocyanic acid. Additionally, the microbes in bioremediation composition may be acid-resistant such that acidic pH adjusting agents can be used in the composition.

Further examples of pH adjustment agents that may be used in some embodiments of the present invention include various bases, which may be weak bases or strong bases. A strong base is defined as an acid that completely disassociates in water, whereas a weak base does not. Examples of strong bases include, but are not limited to, the hydroxides of Group I and Group II metals, for example, LiGH, NaOH, KOH and RbOH. Examples of weak bases include, but are not limited to, alanine, ammonia and methylamine. Still further examples include various carbonates, such as calcium carbonate and sodium bicarbonate.

As used herein the terms "buffer" and "buffer solution" refer to aqueous solutions comprising a mixture of a weak acid and its conjugate base or a weak base and its conjugate acid. The pH of a buffer changes very little when a small amount of strong acid or base is added to it and thus it is used to prevent changes in the pH of a solution. This is important in a number of applications, for example, in chemical systems or mixtures comprising enzymes and/or microbes wherein the viability, productivity, and/or activity of the enzymes and/or microbes are extremely pH dependent.

As used herein, the term "enzyme" refers to any of numerous proteins that cause chemical reactions. In some embodiments of the present invention enzymes used may include, but are not limited to, oxidoreductases, transferases, hydrolases, lyases, isomerases and ligases. An oxidoreductase catalyzes oxidation/reduction reactions and/or transfers hydrogen and/or oxygen atoms or electrons from one substance to another. Examples of oxidoreductases include dehydrogenase and oxidase. A transferase transfers a functional group from one substance to another, for example methyl, acyl, amino, or phosphate groups. Examples of transferases include transaminase and kinase. A hydrolase results in the formation of two products from a substrate by hydrolysis. Examples of hydrolases include lipase, amylase, and peptidase. A lyase results in the non-hydrollytic addition or removal of groups from substrates. A lyase reaction may result in the cleavage of C—C, C—N, C—O, and/or C—S bonds. An example of a lyase includes decarboxylase. An isomerase results in intramolecular rearrangements within a single molecule. Examples of isomerases include isomerase and mutase. A ligase joins two molecules by synthesis of new C—O, C—S, C—N and/or C—C bonds with the simultaneous breakdown of ATP. An example of a ligase includes synthetase.

Further examples of enzymes that may be used in some embodiments of the present invention include, but are not limited to, catalases, glucose oxidases, laccases, fructosyltransferases, glucosyltransferases, amylases, cellulases, lipases, mannanases, pectinases, phytases, proteases, pullulanases, xylanases, pectate lysases, alpha-acetolactate decarboxylases, and glucose isomerases.

As used herein, the term "microbe" refers to bacteria, yeast, fungi, algae, protozoa, and combinations thereof. In some embodiments of the present invention, naturally occurring microbes may be used. Alternatively, genetically engineered microbes may be used. Bacteria that may be used in some embodiments of the present invention may be aerobic such as *Pseudomonas, Alcaligenes, Sphingomonas, Rhodococcus*, and *Mycobacterium*. In some other embodiments the bacteria utilized may be anaerobic. In yet another example, the bacteria utilized may be methylotrophs, or bacteria that utilize methane for carbon and energy. An example of a bacterium that may be utilized in the present invention includes, but is not limited to, *Pseudomonas putida* which is a gram-negative soil bacterium that can digest toulene, a component of paint thinner. It is also capable of degrading naphthalene, a product of petroleum refining, in contaminated soils as described in U.S. Pat. No. 5,536,407 to Petersen, which is incorporated by reference herein in its entirety herein. Another example is *Dechloromonas aromatic*, a soil bacteria genus which is capable of degrading perchlorate and *aromatic* compounds. Further examples of bacteria include *Nitrosomonas europaea, Nitrobacter hamburgensis*, and *Paracoccus denitrificans* which are capable of digesting contaminants found in industrial waste water. Most waste water treatment systems rely on microbial activity to remove unwanted mineral nitrogen compounds (e.g., ammonia, nitrite, nitrate). The removal of nitrogen is a two stage process that involves nitrification and denitrification. During nitrification, ammonium is oxidized to nitrite by organisms like *Nitrosomonas europaea*. Then, nitrite is further oxidized by microbes like *Nitrobacter hamburgensis*. In anaerobic conditions, nitrate produced during ammonium oxidation is used as a terminal electron acceptor by microbes like *Paracoccus denitrificans*. The result is dinitrogen gas. Through this process, ammonium and nitrate, two pollutants responsible for eutrophication in natural waters, are remediated.

A further example of a bacterium that may be employed in some embodiments of the present invention is *Deinococcus radiodurans* which is a radiation-resistant extremophile bacterium that is genetically engineered for the bioremediation of solvents and heavy metals. A further example of a bacterium that may be utilized in some embodiments of the present invention is *Methylibium petroleiphilum* which is capable of digesting methyl tert-butyl ether (MTBE).

A further example of a bacterium utilized in the present invention *Nitrosomonas europea*. Trihalomethane(s) (THM) contaminated water may be remediated through metabolism of *Nitrosomonas europea*. Yet another example of a bacterium that may be utilized in some embodiments of the present invention is *Methylibium petroleiphilum*, which is capable of completely mineralizing MTBE. *Methylibium petroleiphilum* is capable of consuming a diverse range of gasoline derivatives as its sole carbon source, including: methanol, ethanol, toluene, benzene, ethylbenzene, and dihydroxybenzenes.

Still further embodiments of the present invention may utilize bacteria from the genus *Bacillus*. For example, species from the *Bacillus* genus that may be used include, but are not limited to, *B. alcalophilus, B. alvei, B. aminovorans, B. amyloliquefaciens, B. aneurinolyticus, B. anthracis, B. aquaemaris, B. atrophaeus, B. benzeovorans, B. boroniphilus, B. brevis, B. caldolyticus, B. centrosporus, B. cereus, B. circulans, B. coagulans, B. firmus, B. flavothermus, B. fusiformis, B. globigii, B. infernus, B. larvae, B. laterosporus, B. lentus, B. licheniformis, B. megaterium, B. mesentericus, B. mucilaginosus, B. mycoides, B. natto, B. pantothenticus, B. polymyxa, B. pseudoanthracis, B. pumilus, B. schlegelii, B. sphaericus, B. sporothermodurans, B. stearothermophilus, B. subtilis, B. thermoglucosidasius, B. thuringiensis, B. vulgatis*, and *B. weihenstephanensis*.

Still further embodiments of the present invention may utilize bacteria from the genus *Micrococcus*. For example, species from the *Micrococcus* genus that may be used include, but are not limited to, *M. antarcticus, M. agilis, N, cohnii, M. endophyticus, M. flavus, M. halobius, M. kristinae, M. lactis, M. luteus, M. lylae, M. nishinomiyaensis, M. mucilaginosus, M. roseus, M. mortus, M. sedentarius, M. terreus, M. varians*, and *M. yunnanensis*.

U.S. Pat. No. 5,990,067 to Franssen et al. and U.S. Pat. No. 7,459,421 to Bullis et al., both of which are incorporated by reference herein in their entireties, disclose dry compositions for treating contaminated concrete surfaces, wherein the compositions optionally include microorganisms including bacteria. Also, incorporated by reference in their entireties, for written description and enablement purposes, are the following patents and applications on points related to the use of bacteria for bioremediation: U.S. Pat. Nos. 5,508,194; 6,503,746; 8,444,962; 5,939,086; 5,464,766; 5,536,407; U.S. Patent Application Publication Nos. 2010/0274069; 2003/0100098; 2012/0094360; PCT Application Nos. WO 94/29242; WO 95/08513; WO 99/66080; WO 2005/042724; WO 2006/018306.

In some embodiments of the present invention, the bioremediation composition includes a form of silicate. The silicates are divided into different classes by their structures, such as, hydrous aluminum silicates or phyllosilicates, which can be used in the bioremediation compositions. Zeolite, clinoptilolite, and other members of the Zeolite family including any within the framework of silicates having an exchanging cation, for example, amicite, shabazite, pistilbite, ferrierite, gobbinisite and mazzite, are absorptive or absorbing agents. Zeolite's color combined with the other ingredients gives it coloration without the use of artificial pigments. Zeolite has a chemical name of potassium-calcium-sodium-aluminosilicate. One producer of this is Bear River Zeolite Corporation, in Thompson Falls, Montana. It is part of the hydrous aluminum silicates chiefly found in igneous rocks and characterized by a ready loss or gain of water. Zeolites are used as molecular sieves to separate mixtures because they are capable of selective absorption and are a microporous material that is capable of absorbing and encapsulating other agents. One of Zeolites' functions is similar to that of microorganisms, but instead of digesting contaminants, it imprisons them. They have a high ion exchange capacity and can be used to separate petrol, benzene, and toluene from low grade raw materials, such as, coal and methanol.

Additionally, the following patents are incorporated by reference for further enablement and disclosure: U.S. Pat. No. 7,071,153 to Lewis et al.; U.S. Pat. No. 6,969,699 to Sen et al.; U.S. Pat. No. 7,658,805 to Netherton; U.S. Pat. No. 8,206,062 to Hoag et al.; U.S. Pat. No. 6,511,954 to Wilbur et al.; U.S. Pat. No. 8,197,605 to Laffitte et al.; and U.S. Pat. No. 8,133,855 to Dreilinger et al.

Fungi are well-suited for PAH degradation and higher molecular weight substances. They also function well in non-aqueous environments where hydrophobic PAHs accumulate; a majority of other microbial degradation occurs in aqueous phase. They can function in the very low-oxygen conditions.

A specific example of a fungus that may be utilized in some embodiments of the present invention is the lignin-degrading white rot fungus, *Phanerochaete chrysosporium*, which exhibits a strong potential for the bioremediation of pesticides, polyaromatic hydrocarbons, PCBs, dioxins, dyes, TNT and other nitro explosives, cyanides, azide, carbon tetrachloride, and pentachlorophenol. White rot fungi degrade lignin with nonselective extracellular peroxidases, which can also facilitate the degradation of other compounds containing similar structure to lignin within the proximity of the enzymes released.

Other examples of fungi that may be used in some embodiments of the present invention include *Armillaria, Heterobasidion annosum, Serpula lacrymans, Lenzites trabea, Fibroporia vaillentii*, and *Sporotrichum pulverulentum*.

Also, incorporated by reference in their entireties on points related to the use of fungi for bioremediation for written description and enablement purposes are the following: U.S. Pat. Nos. 5,476,788; 5,486,474; PCT Application Publication No. WO 2006/136177. Also, incorporated by reference in their entireties on points related to the use of fungi and bacteria for bioremediation for written description and enablement purposes are U.S. Pat. No. 6,194,197 and PCT Application Publication No. WO 00/41976.

In some embodiments of the present invention, yeast may be used in a bioremediation composition and/or method to remove contaminants from a solid or a liquid. Yeasts are eukaryotic microorganisms classified in the kingdom Fungi, with 1,500 species currently described (estimated to be 1% of all fungal species). One example of a yeast that may be used in some embodiments of the present invention is *Yarrowia lipolytica* which is capable of degrading palm oil and mill effluent, TNT, and other hydrocarbons such as alkanes, fatty acids, fats and oils.

As used herein, the term "nutrient" refers to any chemical compound or matter that provides the material needed to enable microbe metabolism, growth, viability and productivity. As with any other living organism, microbes such as bacteria, fungi and yeast require nutrients to survive. For example, microbes require a carbon source, which can be obtained from, sugars, alcohols and other organics. However, microbes also require a source of nitrogen, amino acids, various salts and essential elements in order to grow and metabolize normally. Further examples of nutrients may include, but are not limited to, agar, starch, sugars, molasses, yeast extract, corn-steep liquor, spent fermentation mash, dried distiller grain solids (DDGS), milled corn, corn flour, cotton hulls, wheat straw, corn stover, rice, grains, leaves, dung, manure, residential yard waste, bagasse, bark, saw dust, and wood chips.

As used herein, the term "densification agent" refers to any solid or liquid additive that raises the bulk density of a first mixture, when the densification agent is added to and mixed with the first mixture. As used herein, the term "binding agent" refers to any solid or liquid material that assists with binding together two or more components of a mixture. A binding agent, among other things, may be utilized to assist with transporting a mixture from one point to another, assist with the application of a composition to a target area, surface, solid, liquid, etc., and assist with dust control and/or mitigation.

As used herein, a "visual aid" refers to any solid or liquid material that when added to a first mixture provides improved visual contrast between the second resultant mixture and the environment to which the second mixture is applied. For example, a visual aid may comprise a black powder, applied to a white first mixture, such that the resultant second mixture is gray, so that when the gray mixture is applied to a white surface, it can be more easily recognized, thus insuring that appropriate and/or complete coverage of the area to be treated has been attained. A visual aid may comprise a dye, ink, pigment, bioluminescent bacteria, and combinations thereof. The term "dye" refers to a colorant, usually transparent, which is soluble in an application medium. The term "ink" refers to a liquid or paste containing various pigments and/or dyes used for coloring a surface to produce an image, text, or design. The term "pigment" refers to a synthetic or natural (biological or mineral) material that changes the color of reflected or transmitted light as the result of wavelength-selective absorption. Further examples of visual aids are carbon black and fumed silica.

A bioluminescent bioreporter is an organism that is genetically engineered to produce light when a particular substance is metabolized. For example, bioluminescent (lux) transcriptional gene fusions may be used to develop light emitting reporter bacterial strains that are able to sense the presence, bioavailability, and biodegradation of organic chemical pollutants such as naphthalene, toluene, and isopropylbenzene. In general, the lux reporter genes are placed under regulatory control of inducible degradative operons maintained in native or vector plasmids or integrated into the chromosome of the host strain. Bioluminescent microorganisms are disclosed in U.S. Patent Publication No. 2007/0002994 to Simpson et al., which is incorporated by reference herein in its entirety.

Due to the widespread use of petroleum products and the current regulations requiring underground storage tanks to be upgraded, replaced or closed, the number of petroleum-contaminated sites has abounded. Of particular concern for drinking water quality are the more water-soluble components, benzene, toluene, ethylbenzene and xylenes (BTEX). Natural attenuation which relies on in situ biodegradation of pollutants has received a large amount of attention especially for petroleum contaminants. While microorganisms capable of biodegradation of BTEX compounds are usually present at these sites, there is a need to know whether or not conditions are favorable for biodegradation to occur.

Bioluminescent reporters have been widely used for the real time non-destructive monitoring of gene expression. Heitzer et al. (1992) developed a quantitative assay for naphthalene bioavailability and biodegradation using a nah-lux reporter strain HK44 constructed by King et al. (1990) containing a lux transposon (Tn4431) insertion in nahG of the lower naphthalene degradation operon. The nah-lux reporter was expanded for use as an online optical biosensor for application in groundwater monitoring (Heitzer et al., 1994). Other lux fusions have been constructed for monitoring the expression of catabolic genes including those for degradation of isopropylbenzene (Selifonova et al., 1996) and toluene (Applegate et al., 1997).

As used herein, the term "biocatalyst" refers to any enzyme, microbe, protein, amino acid, nucleic acid, fat, lipid or mixture thereof which is capable of interacting or reacting with contaminants, or is capable of increasing the decomposition and/or degradation rates of contaminants.

An aspect of the present invention includes a composition for the remediation of contaminated soils or water supplies comprising an oxide phase, a silicate phase, a pH adjustment agent, a densification agent, a nutrient, a surfactant, and a biocatalyst.

In some embodiments of the present invention, the oxide phase may comprise silica, alumina, iron (II) oxide, iron (II,III) oxide, iron (III) oxide, iron (III) oxide trihydrate, calcium oxide, magnesium oxide, potassium oxide, and/or combinations thereof. In further embodiments, the oxide phase may comprise silica, alumina, iron (III) oxide, and/or calcium oxide. In various embodiments of the invention, the oxide phase may comprise diatomaceous earth (also known Celite, diatomite, and kieselguhr), which typically comprises about 80 to 90% silica, about 2 to 4% alumina, and about 0.5 to 2% iron oxide. Diatomaceous earth is naturally occurring sedimentary rock that is easily crumbled into a fine white powder, with a typical particle size in the 10 to 200 μm range. In one embodiment of the present invention, the oxide phase may include Brownmillerite, which typically comprises a mixture of calcium oxide, alumina, and iron oxide.

In still further embodiments of the invention, the oxide phase may comprise fly ash. Fly ash provides the advantage of being readily available from the electrostatic precipitators and bag filters of coal-fired power plants because fly ash is a waste product from thermal power stations. Thus, the present invention provides an outlet and use for an industrially produced by-product stream. A second advantage is that fly ash is generally in particulate form consisting of very small sizes, e.g., 0.5 μm to 300 μm. The small size provides an extremely large amount of surface area per unit mass, which facilitates better contacting of the fly ash with the other components in the composition of the present invention, as well as with the target contaminants, which in turn increases the rates of the decontamination reactions. Pulverized fly ash, which is used in some embodiments, is typically made of 95% oxides of silicon, aluminum, and iron. The remaining 5% is often unburnt coal and oxides of titanium, potassium, calcium, and other metal oxides. In additional embodiments, cenospheres, which are hollow spherical particles with a similar size range as fly ash, can be used with fly ash or in the place of fly ash; however, using cenospheres will increase the price of the final bioremediation composition. In some embodiments, the fly ash is washed with water and dried before it is added to the bioremediation composition.

In some embodiments of the present invention, the silicate phase may comprise Belite ($Ca_2SiO_4$), Alite ($Ca_3O \cdot SiO_4$), tricalcium silicate ($Ca_3SiO_5$), and/or combinations thereof. In some embodiments the silicate phase may comprise at least one of cement kiln dust, cement, sol gels, and combinations thereof. In still further embodiments of the present invention, the silicate phase may comprise cement kiln dust. In still further embodiments of the present invention, the silicate phase may comprise Portland cement kiln dust. Cement kiln dust is an advantageous raw material as it is regularly collected in efforts to mitigate emissions from cement kilns. Thus, this source of silicate provides an outlet for an industrially generated by-product stream. Also, like the fly ash described above, kiln dust comprises a distribution of very small particles, with the largest kiln dust particles rarely exceeding 0.3 mm. These small particle sizes provide an extremely large amount of surface area per unit mass, which facilitates better contacting of the kiln dust with the other components in the composition of the present invention, as well as with the targeted contaminants. This in turn increases the rates of the decontamination reactions. In still further embodiments of the present invention, the silicate phase may include any known calcium containing silicate mineral, as known by one of ordinary skill in the art.

In some embodiments of the present invention, the pH adjustment agent may include at least one of an acid, a base, and a carbonate. In further embodiments of the present invention, the pH adjustment agent may comprise calcium carbonate. Calcium carbonate is a convenient, readily available, and cost effective pH adjustment agent as it is commonly found in rock all around the world, including, but not limited to limestone, chalk, marble, and travertine. An additional advantage is that these calcium carbonate containing rocks are relatively soft and are readily comminuted and reduced to powder form. Finally, because many naturally occurring bacteria prefer neutral or basic conditions, calcium carbonate with a pH value of 9.4 is effective at providing powder compositions for bioremediation that can elevate the pH of the bioremediation composition as well as the pH of the targeted contamination site.

In various embodiments of the invention, the composition may further include one or more of metal, baking soda, bioluminescent materials, perfumes, charcoal, odor absorbing compounds, and clay. In one embodiment, clay is added to the composition to improve the abrasive action of the fly ash and/or to change the color of the composition, e.g., lighten the color of the composition.

In some embodiments of the present invention, the densification agent may comprise at least one of a powder, a dust, a shaving, a particulate, and combinations thereof, and wherein the densification agent has a particle density of greater than about 1.5 g/cm$^3$, greater than about 2.0 g/cm$^3$, greater than about 2.5 g/cm$^3$, or greater than about 3.0 g/cm$^3$. In some embodiments of the present invention, the densification agent may have a particle density in the range from about 1.5 g/cm$^3$ to about 5.0 g/cm$^3$. As used herein, the term "particle density" refers to the density of the solid excluding the interstitial volume between individual particles. Including this empty volume contribution results in a material's bulk density. Therefore, the bulk density for a powder will be less than (or equal to if there is no interstitial space) the particle density. In some further embodiments of the present invention, the densification agent may comprise a metal, a plastic, a mineral, and combinations thereof. In still further embodiments of the present invention, the densification agent may comprise sand. In one embodiment of the invention, the sand used as a densification agent may comprise Andesite, a type of wicking sand, ground quartz, powdered quartz, or whatever is readily and economically available in a given geographic area. In some embodiments of the present invention, the sand used as a densification agent, may comprise a particles size in the range from about 100 microns to about 1000 microns. The purpose of the densification agent is to provide the remediation composition with a bulk density that is sufficiently high to enable efficient application of the composition to the surface, area, volume, etc. that is targeted for treatment. It will be known to one skilled in the art that the application of low density powders such as carbon black and fumed silica is extremely difficult, especially if the application is in an open environment subject to variable air flow. Wind losses of the bioremediation product result in the higher application and bioremediation costs. A densification agent alone, or in combination with a binding agent, will reduce such product losses and increase the efficiency of the bioremediation process.

In further embodiments of the present invention, the composition may further comprise a binding agent. Without intending to be bound by theory, a binding agent may provide binding characteristics, wherein two or more components of the composition are attracted to each other, by differences in surface tension, viscosity, charge, polarity, and combinations thereof. Examples of binding agents include, but are not limited to, water, polysaccharides, starches, gums, acaia, alginic acid, carboxymethylcellulose, ethylcellulose gelatin, liquid glucose, methylcellulose, povidone, and pregelatinized starch. Examples of gum binding agents include, but are not limited to, cordial, okra gum, *Cassia roxburghii* seeds gum, gum Arabic, gum ghatti, ghum tragacanth, and other common gums. In some embodiments of the present invention, the binding agent may comprise a construction material, for example a mortar, a paste, a grout, and combinations thereof. As used herein, the term "grout" refers to an emulsified mixture comprising water, cement, and sand. A grout may also include fine gravel and a coloring agent. Thus, when a colored grout is used as the binding agent, the grout may also serve the purpose of a visual aid.

In some embodiments of the present invention, the composition may further comprise a visual aid selected from the group consisting of a dye, ink, pigment, bioluminescent bacteria, and combinations thereof. In further embodiments of the present invention, the visual aid may be selected from the group consisting of carbon black, fumed silica and combinations thereof. In one embodiment, an indicator, such as a color-change-based indicator can be included in the bioremediation composition. The color-change-based indicator may make the bioremediation composition one color initially and then change colors once the area to be cleaned is clean. Additionally, developers could also be added to the bioremediation composition depending on the type of indicator used. For example, if the indicator is phenolphthalein, the developer can be an acid or a base depending upon whether the indicator is used in an acidic or basic substrate. Indicators and developers similar to those disclosed in U.S. Pat. No. 6,814,816 to Archar et al., which is incorporated by reference herein in its entirety, can be used in some embodiments.

In some embodiments of the present invention, the surfactant may comprise at least one of a nonionic surfactant, a cationic surfactant, an anionic surfactant, an amphoteric surfactant, and combinations thereof.

In some embodiments of the present invention, the biocatalyst may comprise at least one of an enzyme, a bacterium, a fungus, a yeast, and combinations thereof. In some embodiments of the present invention, the biocatalyst may comprise at least one bacterium from the *Bacillus* genus, the *Micrococcus* genus, and combinations thereof.

An aspect of the present invention is a composition for remediation of contaminated liquids or solids comprising an oxide phase between about 20 wt % and about 40 wt %, a silicate phase between about 5 wt % and about 25 wt %, a pH adjustment agent between about 1 wt % and about 20 wt %, and a densification agent between about 1 wt % and about 20 wt %. The composition further comprises a nutrient between about 1 wt % and about 10 wt %, a surfactant between about 1 wt % and about 10 wt % and a biocatalyst between about 10 wt % and about 30 wt %.

In some embodiments of the present invention, the composition may further comprise a visual aid between about 0.1 wt % and about 10 wt %. In some embodiments of the present invention, the composition may further comprise a binding agent between about 0.1 wt % and about 10 wt %.

In some embodiments of the present invention, the composition may comprise a powder with a particle size of less than 0.125 inches. In some embodiments of the present invention, the composition may comprise a powder with a particle size of less than 0.0625 inches. In some further embodiments of the present invention, the composition may comprise a powder with a particle size of less than 1000 microns. In some further embodiments of the present invention, the composition may comprise a powder with a particle size of less than 100 microns.

In some embodiments of the present invention, the composition may comprise a moisture content of less than 20 wt % water. In some embodiments of the present invention, the composition may comprise a moisture content of less than 15 wt % water. In some further embodiments of the present invention, the composition may comprise a moisture content of less than 10 wt % water. In some further embodiments of the present invention, the composition may comprise a moisture content of less than 5 wt % water.

An aspect of the present invention is a composition for remediation of contaminated liquids or solids comprising between about 20 wt % and about 40 wt % fly ash, between about 10 wt % and about 20 wt % Portland cement kiln dust, between about 5 wt % and about 15 wt % sand, between about 0.5 wt % and about 4 wt % milled whole kernel corn, between about 0.5 wt % and about 4 wt % milled cotton hulls, between about 5 wt % and about 15 wt % calcium carbonate, between about 2 wt % and about 10 wt % grout, between about 1 wt % and about 10 wt % detergent, and between about 10 wt % and about 30 wt % of biocatalyst. The biocatalyst comprises a composition of between about 5 wt % and about 15 wt % *Bacillus amyloliquefaciens*, between about 5 wt % and about 15 wt % *Bacillus atrophaeus*, between about 5 wt % and about 15 wt % *Bacillus benzeovorans*, between about 5 wt % and about 15 wt % *Bacillus cereus*, between about 5 wt % and about 15 wt % *Bacillus licheniformis*, between about 5 wt % and about 15 wt % *Bacillus megaterium*, between about 20 wt % and about 25 wt % *Bacillus subtilis*, between about 5 wt % and about 15 wt % *Bacillus polymyxa*, between about 5 wt % and about 15 wt % *Micrococcus flavus*, and between about 5 wt % and about 15 wt % *Micrococcus conglomeratus*. The solid remediation composition may further comprise a particle size of less than 0.125 inches.

One embodiment of the present invention includes a composition for remediation of contaminated liquids or solids which may comprise about 31 wt % fly ash, about 16 wt % Portland cement kiln dust, about 10 wt % sand, about 2 wt % milled whole kernel corn, about 2 wt % milled cotton hulls, about 10 wt % calcium carbonate, about 4 wt % colored grout, about 5 wt % detergent, and about 20 wt % of biocatalyst. The biocatalyst may comprise about 9.1 wt % *Bacillus* amyloliquefaciens, about 9.1 wt % *Bacillus atrophaeus*, about 9.1 wt % *Bacillus benzeovorans*, about 9.1 wt % *Bacillus cereus*, about 9.1 wt % *Bacillus licheniformis*, about 9.1 wt % *Bacillus megaterium*, about 18.5 wt % *Bacillus subtilis*, about 9.1 wt % *Bacillus polymyxa*, about 9.1 wt % *Micrococcus flavus*, and about 9.1 wt % *Micrococcus conglomeratus*. One skilled in the art will recognize that obtaining precise percentage contributions in the composition, for any of the microbes listed above, is difficult and that some natural variability will occur around the preferred target values. Therefore, compositions with microbe concentrations that fall within a reasonable variability range, for example due to the method of producing the biocatalyst, are intended to fall within the scope of the present invention. One skilled in the art will recognize that a microbe composition may also include residue (e.g., growth media) from the microbe manufacturing steps. In some embodiments of the present invention, the biocatalyst compositions describe above may contain from about zero weight percent up to about 75 wt % residual growth media.

Some embodiments of the invention include a composition for the bioremediation of contaminated solids or liquids comprising about 31 wt % fly ash; about 16 wt % kiln dust; about 10 wt % sand; about 10 wt % calcium carbonate; about 5 wt % detergent; about 4 wt % grout; about 2 wt % corn; about 2 wt % cotton; and about 20 wt % of a biocatalyst mixture comprising: about 9 wt % *Bacillus amyloliquefaciens*; about 9 wt % *Bacillus atrophaeus*; about 9 wt % *Bacillus benzeovorans*; about 9 wt % *Bacillus cereus*; about 9 wt % *Bacillus licheniformis*; about 9 wt % *Bacillus megaterium*; about 19 wt % *Bacillus subtilis*; about 9 wt % *Bacillus polymyxa*; about 9 wt % *Micrococcus flavus*; and about 9 wt % *Micrococcus conglomeratus*.

In some embodiments of the present invention, the bioremediation composition consists of a two-part formulation, wherein a first part consisting of all of the remaining non-biocatalyst components, e.g., oxide phase, a silicate phase, a pH adjustment agent, a densification agent, a nutrient, a surfactant, binding agent, and visual aid, and a second part consists of the biocatalyst with or without residual growth media. In some embodiments of the present invention, a mass ratio of the second part to the first part may be in the range from about 0.1 to 1.0, to about 10 to 1.0.

In some embodiments of the present invention, the solid bioremediation composition may be converted to a liquid formulation by mixing with water. In some embodiments of the present invention, about one pound of the solid bioremediation composition is mixed with about one gallon of water, resulting in a final liquid form bioremediation product. In some embodiments of the present invention, a ratio of the composition to liquid water is in the range of about 0.1 pounds of solid to about one gallon of water, to about 10 pounds of solid to about one gallon of water.

The following paragraphs describe methods to manufacture the compositions of the present invention, in order to enable one of ordinary skill in the art to make and use such compositions. For powder and/or granular compositions, various methods known to one of ordinary skill in the art may be used. In some embodiments of the present invention, the desired composition can be achieved by individually weighing out each component followed by transfer to an industrial mixer or blender, wherein they are subsequently blended. So, any of the components of the remediation composition, e.g., oxide phase, silicate phase, pH adjustment agent, densification agent, nutrient, surfactant, and biocatalyst, may be mixed together using an industrial mixer or blender. In some embodiments of the present invention, the mixer or blender may be positioned on a weigh-scale and/or weigh-cells, so that each component can be added directly to the mixing device, thus eliminating a separate weigh step and transfer step, and thus providing a more reliable and accurate batching process. Examples of blenders and mixers that may be used to formulate the compositions of the present invention include, but are not limited to, ribbon blenders, V-blenders, cone screw blenders, screw blenders, double cone blenders, planetary mixers, dispersion mixers, counter-rotating mixers, paddle mixers, jet mixers, drum blenders, Banbury mixers, and combinations thereof.

Mixing may be achieved in a batch mixing process or in a continuous process. A single mixing device may be used, or two or more in series and/or in parallel may be used. The various solid components may be added using standard means known to one of ordinary skill in the art, for example single-screw or twin-screw extruders. In addition, the mixers may or may not provide temperature and pressure controls.

In some embodiments of the present invention, a liquid processing aid may be used to facilitate more complete and/or faster mixing of the bioremediation composition components. Examples of liquid additives that may be used include water, alcohols and solvents. In some embodiments of the present invention, less than all of the composition components may be mixed in a liquid processing aid, creating an intermediate dispersed phase. After mixing is achieved the liquid processing aid may be evaporated to create a first part of the composition. This may then be subsequently added to a second part of the composition, either during subsequent manufacturing steps, or during the application step to the contaminated area. For example, an oxide phase, a silicate phase, a pH adjustment agent and a densification agent may be mixed together in methanol to create a well mixed dispersion, which is subsequently dried using heat and/or vacuum, to create a first solid part of the composition. A second solid part is separately prepared, in a separate mixer, comprising a nutrient, a surfactant, and a biocatalyst. The two parts may then be added together in a subsequent manufacturing step, or at the contamination site. The concept of a two-part formulation also applies to a system where neither part undergoes a liquid mixing step and/or evaporation step, or where both parts undergo a liquid mixing step and evaporation step. In addition, the composition may comprise more than a two-part formulation, e.g., a three-part formulation or more.

Liquid formulations may be achieved in standard equipment known to one of ordinary skill in the art, in either batch or continuous processes. Such equipment includes for example, stirred-tank reactors, continuous stirred-tank reactors, and static mixers. Mixers for liquid formulation may also include temperature and pressure control systems.

The biocatalyst component may also be manufactured using standard methods and equipment known to one of ordinary skill in the art. In one embodiment of the present invention, for biocatalysts comprising more than one bacterial strain, each strain may be individually grown and subsequently lyophilized. The final desired biocatalyst may then be achieved by mixing the individually lyophilized strains together, at the desired ratios, much like described above for the non-biocatalyst components of the remediation composition. Alternatively, two or more of the bacterial strains may be grown together, provided the optimum growth conditions and media are identified that allow multiple stains to co-exist without outcompeting one another. This approach offers the potential advantage of requiring less fermentation equipment, faster production rates, and lower manufacturing costs. The same principles just highlighted above for growing bacteria, also apply to yeast and fungi.

Various methods of creating the bioremediation composition can be used. In one embodiment, blending of the composition is performed in a paddle mixer at 500 lbs to 1000 lbs mixes. The method comprises creating a microbial mixture; adding fly ash, kiln dust, sand, calcium, sand-colored grout, and detergent to the paddle mixer; mixing these components for at least five minutes to create a first composition mixture; adding cotton, corn, and the microbial mixture to the paddle mixer with the first composition mixture; mixing these components at least five minutes to create the final bioremediation composition; discharging the final bioremediation composition in less than ten minutes; placing the final bioremediation composition in 1-gallon or 5-gallon containers; placing a desiccant bag in the containers with the final bioremediation composition; and sealing the containers to keep the final bioremediation composition from activating.

The following section provides detail regarding methods for applying the remediation composition of the present invention to a contaminated site. Some embodiments of the present invention may comprise in situ and ex situ bioremediation methods of contaminated solids and soils, wherein in situ techniques are defined as those that are applied to soil and groundwater at the site with minimal disturbance. Ex situ techniques are those that are applied to soil and groundwater at the site which has been removed from the site via excavation (soil) or pumping (water).

In one embodiment, a method of ameliorating a contaminated area is provided, comprising: providing a bioremediation composition comprising: between about 20 wt % to about 40 wt % fly ash; between about 10 wt % to about 20 wt % kiln dust; between about 5 wt % and about 15 wt % sand; between about 0.5 wt % and about 4 wt % corn; between about 0.5 wt % and about 4 wt % cotton; between about 5 wt % and about 15 wt % calcium carbonate; between about 2 wt % and about 10 wt % grout; between about 1 wt % and about 10 wt % detergent; and between about 10 wt % and about 30 wt % of a biocatalyst mixture; spreading an effective amount of the bioremediation composition onto the contaminated area, wherein the contaminated area comprises a first color characteristic; and providing an effective amount of time in which the bioremediation composition can interact with the contaminated area, wherein after the effective amount of time the contaminated area comprises a second color characteristic, and wherein the second color characteristic is different than the first color characteristic. In a further embodiment, the bioremediation composition further comprises a bioluminescent microbe, and the second color characteristic results from a decrease in bioluminescence associated with the bioremediation composition. In one embodiment, an effective amount of time is at least one day. In a preferred embodiment, an effective amount of time is between two days and 30 days. In a more preferred embodiment, an effective amount of time is between five days and 14 days. In another embodiment, an effective amount of time is five days.

In situ techniques are generally the most desirable options due to lower cost and fewer disturbances to the environment since they provide the treatment in place and avoid excavation and transport of contaminated mass. In situ treatment may be limited by the depth of the soil that can be effectively treated. In many soils effective oxygen diffusion for desirable rates of bioremediation extend to a range of only a few centimeters to about 30 cm into the soil, although depths of 60 cm and greater have been effectively treated in some cases. In some embodiments of the present invention, an in situ technique involves mechanically spreading a solid remediation composition of the present invention onto the contaminated surface. This may be performed using a standard spreader device known to one of ordinary skill in the art. In some embodiments, a single spreading step may complete the application process, wherein all of the components are included in a single formulation. In other embodiments, which use two- or multiple-part formulations, multiple spreading steps may be used. In one embodiment, the bioremediation composition may be rubbed, brushed, or worked into the surface or ground to be cleaned using a mechanical action to work the bioremediation composition into the pours or grains of the surface and/or to spread the bioremediation composition around the contaminated area. In still further embodiments, when applied to solid surfaces, the application of a remediation composition may be subsequently followed by wetting the composition with water. The water may be applied as a spray, using standard methods known to one of ordinary skill in the art. Other liquid wetting agents and wetting formulations may also be used.

Further examples of in situ techniques that may be utilized in some embodiments of the present invention include bioventing, biodegradation, biosparging, and bioaugmentation. Bioventing involves supplying air and nutrients through wells to contaminated soil. In some embodiments of the present invention, pressurized air may be used as a pneumatic carrier gas to transport a solid and/or liquid remediation composition of the present invention to subsurface contamination zones, such as water supplies and aquifers.

In situ biodegradation typically involves supplying oxygen and nutrients by circulating aqueous solutions through contaminated soils to stimulate naturally occurring bacteria to degrade contaminants. It can be used for soil and groundwater. Some embodiments of the present invention may include conditions such as the infiltration of water-containing nutrients and oxygen or other electron acceptors for groundwater treatment, after application of the solid or liquid bioremediation composition of the present invention. The bioremediation composition may be initially applied, for example, by tilling.

In situ biosparging typically involves the injection of air under pressure below the water table to increase groundwater oxygen concentrations and enhance the rate of biological degradation of contaminants by naturally occurring bacteria. Biosparging increases the mixing in the saturated zone and thereby increases the contact between soil and groundwater. The ease and low cost of installing small-diameter air injection points allows considerable flexibility in the design and construction of the system. In some embodiments of the present invention, the pressurized air of a biosparging process may act as a carrier gas to pneumatically convey a powdered and/or liquid remediation composition of the present invention to a subsurface water source, for example an aquifer.

Ex situ techniques typically involve the excavation or removal of contaminated soil from the ground. Examples of ex situ bioremediation techniques that may be used in some embodiments of the present invention include land-farming, composting, biopiles, and bioreactors.

Ex situ landfarming is a technique in which contaminated soil is excavated and spread over a prepared bed and periodically tilled until pollutants are degraded. The goal is to stimulate indigenous biodegradative microorganisms and facilitate their aerobic degradation of contaminants. In general, the practice is limited to the treatment of superficial 10-35 cm of soil. Since landfarming has the potential to reduce monitoring and maintenance costs, as well as clean-up liabilities, it has received much attention as a disposal alternative. In some embodiments of the present invention, the remediation compositions of the present invention may be applied to the prepared beds, in at least one application, followed by periodic tillage. The composition may supplement the indigenous microorganisms, potentially resulting in faster and more complete remediation of the pollutants.

Ex situ composting is a technique that involves combining contaminated soil with nonhazardous organic amendments such as manure or agricultural wastes. The presence of these organic materials supports the development of a rich microbial population and elevated temperature characteristic of composting. Similar to the landfarming example given above, in some embodiments of the present invention, compositions of the present invention may be combined with composting methods to create more effective and faster bioremediation of contaminated sites.

Ex situ biopiles are a hybrid of landfarming and composting. Essentially, engineered cells are constructed as aerated composted piles. Typically used for treatment of surface contamination with petroleum hydrocarbons they are a refined version of landfarming that tend to control physical losses of the contaminants by leaching and volatilization. Biopiles provide a favorable environment for indigenous aerobic and anaerobic microorganisms. The present invention is ideally suited to supplement and improve the bioremediation of contaminants using biopiles.

Examples of bioreactors include slurry reactors or aqueous reactors are used for ex situ treatment of contaminated soil and water pumped up from a contaminated plume. Bioremediation in reactors involves the processing of contaminated solid material (soil, sediment, sludge) or water through an engineered containment system. A slurry bioreactor may be defined as a containment vessel and apparatus used to create a three-phase (solid, liquid, and gas) mixing condition to increase the bioremediation rate of soil-bound and water-soluble pollutants as a water slurry of the contaminated soil and biomass (usually indigenous microorganisms) capable of degrading target contaminants. In general, the rate and extent of biodegradation are greater in a bioreactor system than in situ or in solid-phase systems because the contained environment is more manageable and hence more controllable and predictable. In some embodiments of the present invention, the presently disclosed compositions are used to increase the efficiency and reaction rates of contaminant decomposition reactions in bioreactors.

In some embodiments of the invention, a method of producing a bioremediation composition using biological hosts to synthesize/accumulate bioproducts such as bacteria, eukaryotic microorganisms (e.g., *Saccharomyces cerevisiae*), plants, animal cells (e.g., transformed insect cells growing in culture), and animals is provided. Thus, methods by which effector-sensitive RCANAs can be used to facilitate industrial biosynthesis and bioremediation. For example, provided herein are methods in which effector-dependent ribozymes can be used to (1) control production of a natural product in a biological host, (2) to identify environmental conditions which increase biosynthetic yields, and (3) to isolate strains of a biological host with improved product yields and/or properties. RCANA are more robust than allosteric protein enzymes in several ways: (1) they can be selected in vitro, which facilitates the engineering of particular constructs; (2) the levels of catalytic modulation are much greater for RCANA than for protein enzymes; and (3) because RCANA are nucleic acids, they can potentially interact with the genetic machinery in ways that protein molecules may not.

Various embodiments of the present invention include RCANAs where the catalytic activity of the RCANA is regulated by an effector. The RCANA are, therefore, regulatable in that their activity is under the control of a second portion of the RCANA. Just as allosteric protein enzymes undergo a change in their kinetic parameters or of their enzymatic activity in response to interactions with an effector, the catalytic abilities of the RCANA may similarly be modulated by the effector(s). Thus, some embodiments of the invention are directed to RCANA that transduce molecular recognition into catalysis. Also, RCANAs can be used as regulatory elements to control the expression of one or more genes in a metabolic pathway. RCANAs can also be used as regulated selectable markers to create a selective pressure favoring (or disfavoring) production of a targeted bioproduct.

The methods may include any type of nucleic acid. For example, the methods are not limited to RNA-based RCANA, but also encompass DNA RCANA and RNA or DNA RCANA. Furthermore, the methods can be applied to any catalytic activity the ribozymes are capable of carrying out. For example, the methods are not limited to ligases or splicing reactions, but could also encompass other ribozyme classes. The methods are also not limited to protein or peptide ligands, but also include other molecular species, such as ions, small molecules, organic molecules, metabolites, sugars and carbohydrates, lipids and nucleic acids. The methods may also be extended to effectors that are not molecules, such as heat or light or electromagnetic fields. Furthermore, the methods are not limited to ligand-induced conformational changes, but could also take into account chimeric catalysts in which residues essential for chemical reactivity were provided by both the nucleic acid and the ligand, in concert. Additionally, the effector may be a peptide, a polypeptide, a polypeptide complex, or a modified polypeptide or peptide. The effector may even be, e.g., an enzyme or even light (such as visible light) or even a magnet. The effector may be activated by a second effector that acts on the first effector, which may be an inorganic or an organic molecule. The polypeptide, peptide or polypeptide complex can be either endogenous, i.e., derived from the same cell type as the polynucleotide, or exogenous, i.e., derived from a cell type different than the cell from which the polynucleotide is derived.

In another embodiment of the present invention, a method of detecting an ion in the presence of other ions in a sample is provided. The method comprises: forming a mixture of a nucleic acid enzyme including at least one quencher, a substrate and the sample, to produce a product; and detecting the presence of the product. The substrate is a nucleic acid sequence including a ribonucleotide, at least one quencher and at least one fluorophore. A "nucleic acid enzyme" is a nucleic acid molecule that catalyzes a chemical reaction. The nucleic acid enzyme may be covalently linked with one or more other molecules yet remain a nucleic acid enzyme. Examples of other molecules include dyes, quenchers, proteins, and solid supports. The nucleic acid enzyme may be entirely made tip of ribonucleotides, deoxyribonucleotides, or a combination of ribo- and deoxyribonucleotides.

In another embodiment of the invention, a method of determining the concentration of an ion in the presence of other ions, in a sample, comprising: forming a mixture of a nucleic acid enzyme comprising at least one quencher, a substrate comprising a ribonucleotide, at least one quencher and at least one fluorophore, and the sample, to produce a product; and measuring the amount of product produced.

In various embodiments of the invention, a biosensor, capable of detecting the presence of an ion in the presence of other ions, is provided comprising: a nucleic acid enzyme which includes at least one quencher, and a substrate which includes a ribonucleotide, at least one quencher and at least one fluorophore. A growing number of nucleic acid enzymes have been discovered or developed showing a great diversity in catalytic activity. Many, if not all, of the enzymes are dependent on one or more ion cofactors. In vitro selection may be used to "enhance" selectivity and sensitivity for a particular ion. Such enzymes find particular utility in the compositions and methods of the present invention. For example, nucleic acid enzymes that catalyze molecular association (ligation, phosphorylation, and amide bond formation) or dissociation (cleavage or transfer) are particularly useful. In some embodiments, a nucleic acid enzyme that catalyzes the cleavage of a nucleic acid in the presence of an ion is used. The nucleic acid enzyme may be RNA (ribozyme), DNA (deoxyribozyme), a DNA/RNA hybrid enzyme, or a peptide nucleic acid (PNA) enzyme. PNAs comprise a polyamide backbone and the bases found in naturally occurring nucleosides and are commercially available, e.g., from Biosearch, Inc. in Bedford, Massachusetts. Similar biosensors are described in U.S. Pat. No. 7,906,320 to Lu et al., which is incorporated by reference herein in its entirety.

In certain embodiments, the present invention is directed to a bio-remediate formulation containing Sodium/Calcium Ethylenediaminetetraacetic acid (EDTA), for the cleanup of soil, concrete, asphalt, metal, wood, ceramic, stone, other hard surfaces and including water, that have been contaminated with petroleum hydrocarbons and or mine tailings containing toxic metals. EDTA holds and collects the metals and allows the bio-remediation formula to attack and breakdown the metals that are in petroleum hydrocarbons and mine tailings.

One embodiment is directed to a soil and hard surfaces formulation. By adding 5 to 20% of EDTA to a 500 lbs mix of the present bio-remediation formula. EDTA holds the metal letting the bio-remediate formula attack the metals. Contamination is cleaned up in 30 to 180 days. Using lower percentages of EDTA from 5 to 9% in the bioremediation formula, the bio-remediation time was 180 days. Increasing the EDTA levels 10 TO 14% Butin the same formula, bio-remediation time was decreased to 90 days. Increasing the EDTA levels 15 to 20%, the bio-remediation time was decreased to 30 days.

No difference in increasing the levels of EDTA higher than 20% to the 500 lbs. mix for this application was seen as beneficial.

Tape pull testing may be performed to evaluate the success of the metals bio-remediated.

Another embodiment is directed to a water formulation. The cotton content is preferably increased (ground cotton hulls 90 lbs., and cottonseed meal 50 lbs. and 100 lbs. commercial finally of ground sand, add in 50 lbs. of the bio-remediation formula plus 20% of Sodium/Calcium Ethylenediaminetetraacetic acid) (EDTA), and placing of the formulation in a chemical spill absorbent sock material and or mesh material (in 4 inch, 6 inch, 8 inch, and 12 inch diameter sizes in length), the socks may be used around storm drains.

In water placing chemical resistant flotation devices in the center of the chemical spill absorbent sock material (ranging from 2 inch to 8 inch in size), filled with the EDTA Bio-remediation Formula, gives positive results. The spill sock can also be fastened to flotation buoys as needed to achieve proper water depth. The spill sock allows the water to flow through while collecting the oil/metal or metal contamination and letting the bio-remediation process to begin.

In other embodiments, metals in vehicle fluids are contained in the above-mentioned socks. As motor fluids circulates through vehicle engines, steering, braking, hydraulic and cooling systems picking up heavy metals such as arsenic, lead, cadmium, copper and zinc, as well as other toxins. Main tailings, such as the contamination that entered the Animas River in Colorado in Sep. 8, 2015, can be contained using the present invention.

Various metals, including Arsenic (As), Barium (Ba), Cadmium (Cd), Chromium (Cr), Lead (Pb), Mercury (Hg), Selenium (Se), Silver (Ag) and Thallium (Tl) can also be contained, as well as all the below listed elements/components:

| EPA (the D List) | | |
|---|---|---|
| EPA Hazardous Waste code | Contaminant | Regulated Level (mg/l) (or ppm) |
| D004 | Arsenic (As) | 5.0 |
| D005 | Barium (Ba) | 100.0 |
| D018 | Benzene | 0.5 |
| D006 | Cadmium (Cd) | 1.0 |
| D019 | Carbon Tetrachloride | 0.5 |
| D020 | Chlordane | 0.03 |
| D021 | Chlorobenzene | 100.0 |
| D022 | Chloroform | 6.0 |
| D007 | Chromium (Cr) | 5.0 |
| D023 | o-Cresol | 200.0 |
| D024 | m-Cresol | 200.0 |
| D025 | p-Cresol | 200.0 |
| D026 | Cresol | 200.0 |
| D016 | 2,4-D | 10.0 |
| D027 | 1,4-Dichlorobenzene | 7.5 |
| D028 | 1,2-Dichloroethane | 0.5 |

-continued

| EPA (the D List) | | |
|---|---|---|
| EPA Hazardous Waste code | Contaminant | Regulated Level (mg/l) (or ppm) |
| D029 | 1,1-Dichloroethylene | 0.7 |
| D030 | 2,4-Dinitrotoluene | 0.13 |
| D012 | Endrin | 0.02 |
| D031 | Heptachlor | 0.008 |
| D032 | Hexachlorobenzene | 0.13 |
| D033 | Hexachlorobutadiene | 0.5 |
| D034 | Hexachloroethane | 3.0 |
| D008 | Lead (Pb) | 5.0 |
| D013 | Lindane | 0.4 |
| D009 | Mercury (Hg) | 0.2 |
| D014 | Methoxychlor | 10.0 |
| D035 | Methyl ethyl ketone | 200.0 |
| D036 | Nitrobenzene | 2.0 |
| D037 | Pentachlorophenol | 100.0 |
| D038 | Pyridine | 5.0 |
| D010 | Selenium (Se) | 1.0 |
| D011 | Silver (Ag) | 5.0 |
| D039 | Tetrachloroethylene | 0.7 |
| D015 | Toxaphene | 0.5 |
| D040 | Trichloroethylene | 0.5 |
| D041 | 2,4,5-Trichlorophenol | 400.0 |
| D042 | 2,4,6-Trichlorophenol | 2.0 |
| D017 | 2,4,5-TP (Silvex) | 1.0 |
| D043 | Vinyl Chloride | 0.2 |

All publications, patents, and patent documents cited herein are incorporated by reference herein, as though individually incorporated by reference. The invention has been described with reference to various specific and preferred embodiments and techniques. However, it should be understood that many variations and modifications may be made while remaining within the spirit and scope of the invention.

It is appreciated that certain features of the invention, which are, for clarity, described in the context of separate embodiments, may also be provided in combination in a single embodiment. Conversely, various features of the invention that are, for brevity, described in the context of a single embodiment, may also be provided separately or in any sub-combination.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention.

EXAMPLES

Laboratories produce so-called "ideal" conditions which may be "ideal" for very short times in small-scale situations. However, full-scale, real-life, field work, involves highly variable environments that may be actually more ideal than small-scale systems. The laboratory conditions used to evaluate microbial activities are often irrelevant in the context of real-life remediation conditions. Most commercial microbial applications deal with field conditions not typically found in the laboratory. Many everyday products we currently use are essentially better designed modifications of existing technology. For a product to gain acceptance, it must have new benefits when used in a wide variety of existing conditions. How the product may have performed under rigidly controlled, unchanging laboratory conditions is often a poor prediction of how the product may perform in real-life. However, the following examples are provided to provide further disclosure and enablement:

Example 1: One embodiment of the present invention includes a bioremediation composition with a first part and a second part. The first part may be prepared by mixing the following components:

TABLE 1

| Component | Mass [lb] | % |
|---|---|---|
| Fly ash | 235 | 44.8 |
| Kiln dust | 120 | 22.9 |
| Calcium carbonate | 50 | 9.5 |
| Sand | 50 | 9.5 |
| Milled corn kernels | 10 | 1.9 |
| Milled cotton hulls | 10 | 1.9 |
| Colored grout | 15 | 2.9 |
| Detergent | 35 | 6.7 |
| Total | 525 | 100% |

The corn and cotton hulls may be milled by any suitable method, for example, using a hammer mill. The mixer may be placed on weigh cells, with each component added directly to the mixer, in order to achieve the target mass for each component.

The second part of the bioremediation composition may be manufactured separately from the first part, where the second part comprises a biocatalyst. The biocatalyst can comprise the following components:

TABLE 2

| Component | Mass [lb] | % |
|---|---|---|
| Bacillus amyloliquifaciens | 9.1 | 9.1% |
| Bacillus atophaeus | 9.1 | 9.1% |
| Bacillus benzeovorans | 9.1 | 9.1% |
| Bacillus cereus | 9.1 | 9.1% |
| Bacillus lichenformis | 9.1 | 9.1% |
| Bacillus megarterium | 9.1 | 9.1% |
| Bacillus subtilus | 18.5 | 18.5% |
| Bacillus polymyxa | 9.1 | 9.1% |

TABLE 2-continued

| Component | Mass [lb] | % |
|---|---|---|
| Micrococcus flavus | 9.1 | 9.1% |
| Micrococcus conglomeratus | 9.1 | 9.1% |
| Total | 100 | 100% |

The second part of the composition may be produced by individually growing each species of bacteria in its own separate culture, with growth media optimized for its particular metabolic needs. This may be done using standard methods known to one of ordinary skill in the art of bacterial fermentations, for example, stage-wise culturing to progressively larger fermentation vessels, to produce quantities large enough for large-scale manufacturing processes. After each fermentation is completed, the organisms may be lyophilized to produce large dry master-batches of each individual species. Alternatively, the organisms can be dried using other drying methods now known or later developed. These individual master-batches may then be mixed in a dry mixer, much like the first part, to the desired formulation as specified in Table 2. The completed microbe composition may then be packaged for eventual combination with the first part of the total composition. This may be done in the same mixer used to produce the first part, or in a different mixer. Once the first and second parts have been sufficiently mixed, the complete bioremediation composition may be packaged as needed.

Example 2: Some embodiments of the present invention include a bioremediation composition with the following components:

TABLE 3

| Raw Material | % in Final Product | Substance | % in Raw Material | % in Final Product | Range High (Est.) | Range Low (Est.) |
|---|---|---|---|---|---|---|
| Fly ash | 31 | Silicon dioxide | 60 | 18.6 | 19.5 | 17.7 |
| Fly ash | 31 | Aluminum oxide | 20 | 6.2 | 6.5 | 5.9 |
| Fly ash | 31 | Calcium oxide | 10 | 3.1 | 3.2 | 2.9 |
| Fly ash | 31 | Iron III | 7 | 2.17 | 2.3 | 2.1 |
| Microbial broth | 20 | | 100 | 20 | 21 | 19 |
| Kiln dust | 16 | Calcium oxide | 65 | 10.4 | 10.9 | 9.9 |
| Kiln dust | 16 | Silicon dioxide | 15 | 2.4 | 2.5 | 2.3 |
| Kiln dust | 16 | Sulfur trioxide | 5 | 0.8 | 0.8 | 0.76 |
| Kiln dust | 16 | Aluminum oxide | 4 | 0.64 | 0.6 | 0.57 |
| Kiln dust | 16 | Potassium oxides | 4 | 0.64 | 0.6 | 0.57 |
| Calcium carbonate | 10 | Calcium carbonate | 100 | 10 | 10.5 | 9.5 |
| Sand | 10 | Silicon dioxide | 96 | 9.6 | 10.1 | 9.1 |
| Grout | 4 | Silicon dioxide | 55 | 2.2 | 2.3 | 2.1 |
| Grout | 4 | Calcium oxide | 20 | 0.8 | 0.8 | 0.76 |
| Grout | 4 | Aluminum oxide | 18 | 0.7 | 0.74 | 0.66 |
| Detergent | 5 | Sodium carbonate | 29 | 1.45 | 1.5 | 1.3 |
| Detergent | 5 | Sodium chloride | 29 | 1.45 | 1.5 | 1.3 |
| Detergent | 5 | Acrylic Polymer | 15 | 0.75 | 0.8 | 0.76 |
| Detergent | 5 | Cellulose Gum | 15 | 0.75 | 0.8 | 0.76 |
| Corn | 2 | Corn | 100 | 2 | 2.1 | 1.9 |
| Cotton | 2 | Cotton | 100 | 2 | 2.1 | 1.9 |

The raw product in the first column is comprised of the substances listed in the third column from the left. Thus, the percentage of the substance in the final product is listed in the fifth column. Additionally, a range of the substances' percentages is given in the last two columns on the right.

What is claimed is:

1. A method of treating contaminated soil or water supply, comprising: providing a bioremediation composition comprising: at least one of fly ash and kiln dust, wherein said fly ash is present in said composition at between about 20 wt % and about 40 wt % fly ash; and wherein said kiln dust is present in said composition at between about 10 wt % and about 20 wt % kiln dust; between about 5 wt % and about 15 wt % sand; between about 0.5 wt % and about 4 wt % corn; between about 0.5 wt % and about 4 wt % cotton; between about 5 wt % and about 15 wt % calcium carbonate; between about 2 wt % and about 10 wt % grout; between about 1 wt % and about 10 wt % detergent; between about 10 wt % and about 30 wt % of a biocatalyst mixture; and at least one bioluminescent bioreporter comprising a microbe comprising *Saccharomyces cerevisiae* employing yeast expression vector pYES2, wherein said at least one bioluminescent bioreporter produces light when a substance in said contaminated soil or water supply is metabolized by the at least one bioluminescent bioreporter, spreading an effective amount of the bioremediation composition onto the contaminated soil or water supply, wherein the contaminated soil or water supply comprises a first color characteristic; and providing an effective amount of time in which the bioremediation composition can interact with the contaminated soil or water supply, wherein after the effective amount of time the contaminated soil or water supply comprises a second color characteristic.

2. The method of claim 1, wherein the effective amount of time is at least five days.

3. The method of claim 1, wherein the biocatalyst mixture comprises at least two of the following: *Bacillus amyloliquifaciens, Bacillus atrophaeus, Bacillus benzeovorans, Bacillus cereus, Bacillus lichenformis, Bacillus megarterium, Bacillus subtilus, Bacillus polymyxa, Micrococcus flavus*, and *Micrococcus conglomeratus*.

4. The method of claim 1, wherein at least a portion of the bioremediation composition is contained in a chemical spill absorbent sock material that allows for water to flow through while collecting oil or metal contamination within the sock material.

5. The method as set forth in claim 1, wherein said microbe is able to biodegrade organic chemical pollutants selected from the group consisting of naphthalene, toluene, and isopropylbenzene.

* * * * *